United States Patent
Fukuyama et al.

(10) Patent No.: US 9,147,560 B2
(45) Date of Patent: Sep. 29, 2015

(54) MASS SPECTROMETRY METHOD OF PHOSPHORYLATED PEPTIDES AND SUGAR CHAINS

(71) Applicant: SHIMADZU CORPORATION, Kyoto-shi, Kyoto (JP)

(72) Inventors: Yuko Fukuyama, Kyoto (JP); Koichi Tanaka, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 14/177,993

(22) Filed: Feb. 11, 2014

(65) Prior Publication Data
US 2015/0069226 A1    Mar. 12, 2015

(30) Foreign Application Priority Data

Sep. 9, 2013   (JP) .................................. 2013-186748

(51) Int. Cl.
*H01J 49/40* (2006.01)
*H01J 49/00* (2006.01)

(52) U.S. Cl.
CPC .................................. *H01J 49/0027* (2013.01)

(58) Field of Classification Search
USPC .................................. 250/281, 282, 288, 283
See application file for complete search history.

(56) References Cited

FOREIGN PATENT DOCUMENTS

| | | |
|---|---|---|
| JP | 2008-261824 A | 10/2008 |
| JP | 2009-257844 A | 11/2009 |
| JP | 2012-251914 A | 12/2012 |

OTHER PUBLICATIONS

Fukuyama et al. "An optimized matrix-assisted laser desorption/ionization sample preparation using a liquid matrix, 3-aminoquinoline/alpha-cyno-4-hydroxycinnamic acid, for phosphopeptides", Rapid Communications in Mass Spectrometry, 2012, 26, pp. 2454-2460.*

Fukuyama, Yuko et al., "An optimized matrix-assisted laser desorption/ionization sample preparation using a liquid matrix, 3-aminoquinoline/α-cyano-4-hydroxycinnamic acid, for phosphopeptides", Rapid Communications in Mass Spectrometry, 2012, vol. 26, pp. 2454-2460.

* cited by examiner

*Primary Examiner* — Nicole Ippolito
(74) *Attorney, Agent, or Firm* — Cheng Law Group, PLLC

(57) ABSTRACT

The present invention provides a method for mass spectrometry of phosphorylated peptides or sugar chains, which suppresses the desorption of an unstable site during ionization and achieves high sensitivity (i.e., detects molecular-related ions at a high ionic strength and at a relatively higher ionic strength than other ion species derived from the desorption of an unstable site). A method for mass spectrometry of phosphorylated peptides or sugar chains, the method comprising using, as a liquid matrix, an ionic liquid comprising a 3-aminoquinoline ion and a p-coumaric acid ion. The liquid matrix comprises 3-aminoquinoline and p-coumaric acid, for example, in a molar ratio of 5:1 to 20:1. Ammonium phosphate may be used as an additive.

3 Claims, 3 Drawing Sheets

SEQUENCE LISTING

```
<160> NUMBER OF SEQ ID NOS: 2

<210> SEQ ID NO 1
<211> LENGTH: 16
<212> TYPE: PRT
<213> ORGANISM: bovine
<220> FEATURE:
<221> NAME/KEY: MOD_RES
<222> LOCATION: (3)..(3)
<223> OTHER INFORMATION: PHOSPHORYLATION

<400> SEQUENCE: 1

Phe Gln Ser Glu Glu Gln Gln Gln Thr Glu Asp Glu Leu Gln Asp Lys
1               5                   10                  15

<210> SEQ ID NO 2
<211> LENGTH: 25
<212> TYPE: PRT
<213> ORGANISM: bovine
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (17)..(19)
<223> OTHER INFORMATION: PHOSPHORYLATION

<400> SEQUENCE: 2

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25
```

MASS SPECTROMETRY METHOD OF PHOSPHORYLATED PEPTIDES AND SUGAR CHAINS

BACKGROUND OF THE INVENTION

1. Field of the Invention

The present invention belongs to the fields of medical care, pharmaceutical production, and life science. The present invention relates to the application of MALDI-MS (Matrix-Assisted Laser Desorption/Ionization Mass Spectrometry). More specifically, the present invention relates to a method for mass spectrometry of phosphorylated peptides or sugar chains with the use of a specific ionic liquid matrix.

2. Disclosure of the Related Art

JP 2008-261824 A (Patent Document 1) describes a MALDI mass spectrometry method for analyzing a sugar chain with the use of, as a matrix, an ionic liquid (TMG/CA) comprising an amine (1,1,3,3-tetramethylguanidine) ion and a p-coumaric acid ion.

JP 2009-257844 A (Patent Document 2) describes a MALDI mass spectrometry method for analyzing a mixed sample of a peptide and a sugar chain or a mixed sample of a peptide and a sugar peptide with the use of a mixed liquid matrix prepared by mixing together 3-AQ/CHCA (ionic liquid comprising a 3-aminoquinoline ion and α-cyano-4-hydroxycinnamic acid) as a liquid matrix for peptides and TMG/CA (ionic liquid comprising a 1,1,3,3-tetramethylguanidine ion and a p-coumaric acid ion) as a liquid matrix for sugar chains. More specifically, JP 2009-257844 A describes as follows: a mixed droplet of the above-described mixed liquid matrix and the above-described mixed sample is prepared on a target plate; a solvent is removed and at the same time a spot for mass spectrometry is formed in which 3-AQ/CHCA and TMG/CA are separated from each other and localized; in the central area of the spot in which 3-AQ/CHCA is localized, the peptide ionized by 3-AQ/CHCA is detected, and in the other area, that is, the peripheral area of the same spot in which TMG/CA is localized, the sugar chain or the sugar peptide ionized by TMG/CA is detected.

Rapid Commun. Mass Spectrom. 2012, Vol. 26, pp. 2454-2460 (Non-Patent Document 1) discloses that, as compared to a conventional method using 2,5-dihydroxybenzoic acid (DHB) as a matrix, a 10- to 10,000-fold improvement in sensitivity is achieved by optimizing high-sensitive analysis of a phosphorylated peptide by using 3-AQ/CHCA (3-aminoquinoline ion/α-cyano-4-hydroxycinnamic acid) as a liquid matrix.

Patent Document 1: JP 2008-261824 A
Patent Document 2: JP 2009-257844 A
Non-Patent Document 1: Rapid Commun. Mass Spectrom., 2012, Vol. 26, pp. 2454-2460

SUMMARY OF THE INVENTION

Conventional methods for mass spectrometry of phosphorylated peptides or sugar chains have a problem that desorption of an unstable site is likely to occur during ionization, and therefore analytical sensitivity is insufficient. That is, the problem is that the ionic strength of molecular-related ions, which should be detected, is low, or, even when being high to some extent, the ionic strength of molecular-related ions is relatively lower than those of other ion species (ion species derived from the desorption of an unstable site), and therefore the molecular-related ions cannot be detected. For this reason, there is a demand for a method for mass spectrometry of phosphorylated peptides or sugar chains, which suppresses the desorption of an unstable site and achieves high sensitivity.

An object of the present invention is to provide a method for mass spectrometry of phosphorylated peptides or sugar chains, which suppresses the desorption of an unstable site during ionization and achieves high sensitivity (i.e., detects molecular-related ions at a high ionic strength and at a relatively higher ionic strength than other ion species derived from the desorption of an unstable site).

The present inventors have intensively studied, and as a result, found that the above object of the present invention can be achieved by using, as a matrix, an ionic liquid comprising 3-aminoquinoline ions and p-coumaric acid ions, which has led to the completion of the present invention.

The present invention includes the following.

(1) A method for mass spectrometry of phosphorylated peptides or sugar chains, the method comprising using, as a liquid matrix, an ionic liquid comprising a 3-aminoquinoline ion and a p-coumaric acid ion. The phosphorylated peptide also includes a phosphorylated protein. The sugar chain does not include a sugar peptide and a sugar protein.

(2) The method for mass spectrometry of phosphorylated peptides or sugar chains according to the above (1), wherein the liquid matrix comprising 3-aminoquinoline and p-coumaric acid in a molar ratio of 5:1 to 20:1.

(3) The method for mass spectrometry of phosphorylated peptides or sugar chains according to the above (1) or (2), wherein ammonium phosphate is used as an additive.

A liquid matrix for mass spectrometry comprising an ionic liquid comprising a 3-aminoquinoline ion and a p-coumaric acid ion, which is used as a matrix for mass spectrometry of phosphorylated peptides or sugar chains. The phosphorylated peptide also includes a phosphorylated protein. The sugar chain does not include a sugar peptide and a sugar protein.

The above liquid matrix for mass spectrometry of phosphorylated peptides or sugar chains, which comprises 3-aminoquinoline and p-coumaric acid in a molar ratio of 5:1 to 20:1.

The above liquid matrix for mass spectrometry of phosphorylated peptides or sugar chains, further comprising ammonium phosphate as an additive.

In the present invention, an ionic liquid comprising a 3-aminoquinoline ion and a p-coumaric acid ion is used as a matrix for mass spectrometry. This makes it possible to suppress the desorption of a phosphate group that is an unstable site during ionization of a phosphorylated peptide. As a result, it is possible to detect a molecular-related ion, which should be detected, with high sensitivity, and at a relatively higher ionic strength than other ion species derived from the desorption of a phosphate group as compared to conventional methods. Further, it is possible to suppress the desorption of an acidic sugar, such as sialic acid, and a neutral sugar that are unstable sites during ionization of a sugar chain. As a result, it is possible to detect a molecular-related ion, which should be detected, with high sensitivity, and at a relatively higher ionic strength than other ion species derived from the desorption of unstable sites as compared to conventional methods. Thus, the present invention provides a mass spectrometry method capable of analyzing phosphorylated peptides or sugar chains, which suppresses the desorption of an unstable site during ionization and achieves high sensitivity (detects a molecular-related ion at a high ionic strength, and at a relatively higher ionic strength than other ion species derived from the desorption of an unstable site). Further, the present invention provides a liquid matrix for mass spectrometry comprising an ionic liquid comprising a 3-aminoquinoline ion and a p-coumaric acid ion, which is used as a matrix for mass spectrometry of phosphorylated peptides or sugar chains. The present invention is particularly directed to a MALDI mass spectrometry method.

DETAILED DESCRIPTION OF THE INVENTION

[Liquid Matrix]

Figure 1:
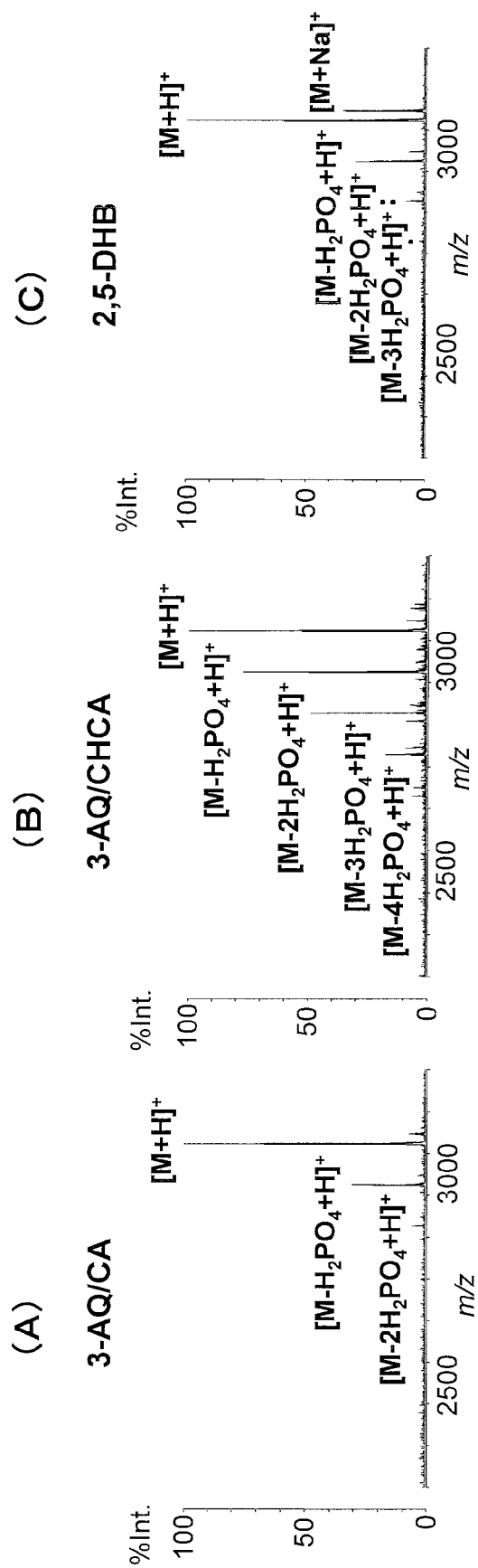
FIG. 1 shows mass spectra of a phosphorylated peptide β-casein 1-25 in a concentration of 10 fmol/μL in positive mode when (A) a liquid matrix 3-AQ/CA was used in Example 1, (B) 3-AQ/CHCA was used as a matrix in Comparative Example 1, and (C) 2,5-DHB was used as a matrix in Comparative Example 1, wherein a horizontal axis represents mass/charge (m/z) and a vertical axis represents a relative ionic strength (% Int.)

The present invention is a method for mass spectrometry of phosphorylated peptides or sugar chains, comprising using, as a liquid matrix, an ionic liquid comprising a 3-aminoquinoline ion and a p-coumaric acid ion. In this specification, the ionic liquid refers to a substance that is present in a liquid state at room temperature and is, in reality, a salt. Examples of the ionic liquid include those comprising an amine ion and an ion of an acid group-containing substance. In the present invention, an ionic liquid (3-AQ/CA) comprising a 3-aminoquinoline (3-AQ) ion and a p-coumaric acid ion (CA) is used as a liquid matrix.

[Object to be analyzed by Mass Spectrometry]

In the present invention, an object to be analyzed by mass spectrometry is a phosphorylated peptide or a sugar chain. The term "phosphorylated peptide" includes a phosphorylated protein. The term "sugar chain" does not include a sugar peptide and a sugar protein.

The phosphorylated peptide (or phosphorylated protein) is not particularly limited, and examples thereof include peptides (or proteins) whose some or all of hydroxyl groups of serine, threonine, and tyrosine residues form a phosphoric ester. Examples of the phosphorylated peptide (or phosphorylated protein) also include peptides (or proteins) whose some or all of aspartic acid, histidine, arginine, and lysine form a phosphoric ester. When some or all of hydroxyl groups of serine, threonine, and tyrosine residues of a peptide (or protein) are phosphorylated, a function of the peptide (or protein) may be changed. When some or all of aspartic acid, histidine, arginine, and lysine of a peptide (or protein) are phosphorylated, a function of the peptide (or protein) may be changed.

During ionization of the phosphorylated peptide (or phosphorylated protein), desorption of a phosphate group is likely to occur. Therefore, it is important for the mass spectrometry of the phosphorylated peptide (or phosphorylated protein) to suppress the desorption of a phosphate group thereby detecting a molecular-related ion, which should be detected, with high sensitivity and at a relatively higher ionic strength than other ion species derived from the desorption of a phosphate group. In the present invention, an ionic liquid comprising a 3-aminoquinoline ion and a p-coumaric acid ion is used as a matrix for mass spectrometry. This makes it possible to suppress the desorption of a phosphate group during ionization of the phosphorylated peptide. As a result, it is possible to detect a molecular-related ion, which should be detected, with high sensitivity and at a relatively higher ionic strength than other ion species derived from the desorption of a phosphate group. As a matter of course, the molecular-related ion that should be detected can be detected at a high S/N ratio. Examples of the phosphorylated peptide (or phosphorylated protein) as an object of mass spectrometry in the present invention also include peptides (or proteins) whose side chain is phosphorylated by artificial modification.

The type of the sugar chain is not limited. During ionization of the sugar chain (especially, an acidic sugar chain such as a sialo-sugar chain or a sulfated sugar chain), desorption of an acid site (e.g., an acidic sugar such as sialic acid, a sulfate group) is likely to occur. Alternatively, desorption of a neutral sugar is also likely to occur. Therefore, it is important for the mass spectrometry of the sugar chain to suppress the desorption of an acid site, such as an acidic sugar (e.g., sialic acid) or a sulfate group, or a neutral sugar, thereby detecting a molecular-related ion, which should be detected, with high sensitivity and at a relatively higher ionic strength than other ion species derived from the desorption of a sugar or a site. In the present invention, an ionic liquid comprising a 3-aminoquinoline ion and a p-coumaric acid ion is used as a matrix for mass spectrometry. This makes it possible to suppress the desorption of an acidic sugar such as sialic acid (or an acid site such as a sulfate group of an acidic sugar) or a neutral sugar during ionization of the sugar chain. As a result, it is possible to detect a molecular-related ion, which should be detected, with high sensitivity and at a relatively higher ionic strength than other ion species derived from the desorption of a sugar or a site. As a matter of course, the molecular-related ion that should be detected can be detected at a high S/N ratio. Therefore, the mass spectrometry method according to the present invention is more suitably used to measure a sugar containing an acidic sugar and/or a neutral sugar. The acidic sugar shall be a sugar having an acidic group such as a sulfate group or a carboxyl group, and one example thereof includes sialic acid.

[Preparation of Liquid Matrix]

A method for preparing the liquid matrix is not particularly limited. A specific preparation method may be implemented in accordance with a conventional ionic liquid preparation method. One of the simplest preparation methods is, for example, a method in which an amine (specifically, 3-aminoquinoline) as a source of amine ions constituting an ionic liquid and an acid substance (specifically, p-coumaric acid) as a source of acidic group-containing substance ions constituting an ionic liquid are mixed and reacted.

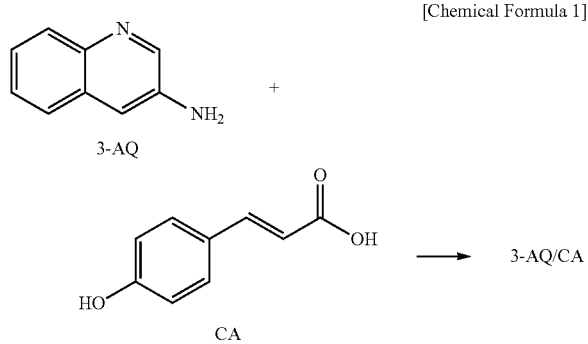

[Chemical Formula 1]

In order to react both the substances, p-coumaric acid may be added to 3-aminoquinoline, or 3-aminoquinoline may be added to p-coumaric acid. The reaction between both the substances can be performed in a solvent. Therefore, at least one of 3-aminoquinoline and p-coumaric acid may be previously prepared as a solution, and then, p-coumaric acid may be added to a 3-aminoquinoline solution, or 3-aminoquinoline may be added to a p-coumaric acid solution. Alternatively, 3-aminoquinoline and p-coumaric acid may be added to a solvent at the same time. The mixing of both the substances can be performed at ordinary temperature.

The ratio between 3-aminoquinoline and p-coumaric acid that should be reacted with each other is not particularly limited. For example, 3-aminoquinoline and p-coumaric acid may be mixed in a molar ratio of 5:1 to 20:1. When an S/N ratio is taken into consideration, there is a case where 3-aminoquinoline and p-coumaric acid are preferably mixed in a molar ratio of 7:1 to 9:1. The concentrations of both the substances to be reacted in a solvent shall be appropriately determined by those skilled in the art.

When the reaction is performed in a solvent, the solvent can be removed after the reaction. The removal of the solvent can be performed by distillation, preferably under reduced pressure. After the removal of the solvent, a liquid substance can be obtained as an ionic liquid. On the other hand, when the solvent used for the reaction can be used also as a matrix solvent (that will be described later), the solvent may not be removed.

When accurately measured, the purity of p-coumaric acid generally sold as a reagent is often about 96%. In the present invention, from the viewpoint of improving analytical sensitivity, p-coumaric acid with a purity of 99% or higher, preferably 99.8% or higher obtained by, for example, purifying p-coumaric acid generally sold as a reagent is preferably used. When p-coumaric acid obtained by purifying commercially-available p-coumaric acid is used, a purification method is not particularly limited and can be appropriately selected by those skilled in the art. For example, such purification can be performed by distillation or recrystallization. Examples of a method for measuring the purity of p-coumaric acid include high-performance liquid chromatography (HPLC), nuclear magnetic resonance (NMR), and the like.

[Formation of Spot for Mass Spectrometry]

When the liquid matrix according to the present invention is used, a droplet of a mixed solution containing the liquid matrix and the object to be analyzed by mass spectrometry (phosphorylated peptide or sugar chain) is formed on a plate for mass spectrometry, and then a solvent is removed (evaporated) to form a spot for mass spectrometry to be irradiated with laser.

The liquid matrix and the object of mass spectrometry (phosphorylated peptide or sugar chain) shall be finally in the form of a mixed solution at the time when a droplet is formed on a plate for mass spectrometry. The droplet of the mixed solution containing the liquid matrix and the object of mass spectrometry (phosphorylated peptide or sugar chain) can be prepared by a pre-mix method or an on-target mix method.

The pre-mix method is a method in which a mixed solution containing the liquid matrix and the object of mass spectrometry (phosphorylated peptide or sugar chain) is previously prepared, and then the mixed solution is dropped onto a plate for mass spectrometry to obtain a droplet of the mixed solution. The mixed solution can be obtained by mixing a solution of the liquid matrix and a solution of the object of mass spectrometry (phosphorylated peptide or sugar chain). These solutions may be mixed, for example, in the same volume.

On the other hand, the on-target mix method is a method in which a solution of the liquid matrix and a solution of the object of mass spectrometry (phosphorylated peptide or sugar chain) are prepared separately, and the respective solutions are then dropped onto the same position in an overlay manner on a plate for mass spectrometry to obtain a droplet of a mixed solution.

As a solvent for the matrix, any conventionally-used solvent can be used without particular limitation. For example, an aqueous solution containing an organic solvent such as acetonitrile, methanol, or ethanol in water may be used. The concentration of the organic solvent in this aqueous solution is, for example, 10% by volume to 90% by volume, preferably 30% by volume to 80% by volume, more preferably 33% by volume to 75% by volume, and one example thereof is about 50% by volume.

As a solvent for the object of mass spectrometry, any conventionally-used solvent can be used without particular limitation. For example, water, or an aqueous solution containing an organic solvent such as acetonitrile, methanol, or ethanol in water may be used. The concentration of the organic solvent in this aqueous solution is, for example, 10% by volume to 90% by volume, preferably 30% by volume to 80% by volume, more preferably 33% by volume to 75% by volume, and one example thereof is about 50% by volume.

The amount of the liquid matrix contained in the droplet of the mixed solution of the liquid matrix and the object of mass spectrometry (phosphorylated peptide or sugar chain) may be, for example, 1 nmol/µL to 10 µmol/µL preferably 10 nmol/µL to 1 µmol/µL. On the other hand, the amount of the object of mass spectrometry (phosphorylated peptide or sugar chain) contained in the droplet of the mixed solution is not particularly limited, but an acceptable amount is, for example, 1 amol to 10 pmol per one mixed droplet.

In the present invention, the liquid matrix preferably contains ammonium phosphate as an additive from the viewpoint of improving analytical sensitivity. Ammonium phosphate shall be finally mixed with the liquid matrix, and may be used by, for example, being dissolved in the above-described matrix solvent. When used, ammonium phosphate shall be contained in the droplet of the mixed solution of the liquid matrix and the object of mass spectrometry (phosphorylated peptide or sugar chain) in a concentration of, for example, 0.01 mM to 100 mM, preferably 0.1 mM to 10 mM, and one example thereof is about 1 mM.

It is to be noted that the volume of the droplet of the mixed solution to be used in order to obtain one spot for mass spectrometry may be, for example, 0.1 µL to 10 µL, preferably 0.5 µL to 1.5 µL, and a specific example thereof may be about 0.5 µL or about 1 µL.

As the plate for mass spectrometry, any plate such as a stainless steel target plate usually used for MALDI mass spectrometry or a chemically or physically surface treated target plate can be used. A plate for mass spectrometry is preferably used which has a well chemically surface treated so that its central part becomes hydrophilic and its peripheral part becomes hydrophobic in order to efficiently remove the solvent from the mixed solution and to obtain a favorable liquid matrix-object of mass spectrometry (phosphorylated peptide or sugar chain) mixed spot for mass spectrometry. Also, a plate for mass spectrometry is preferably used which is subjected to physical surface treatment, such as polishing treatment or mirror finish, so that its surface has desired surface roughness.

[Mass Spectrometer]

A mass spectrometer to be used in the present invention is not particularly limited as long as the mass spectrometer is combined with a MALDI (Matrix-Assisted Laser Desorption/Ionization) ion source. Examples of such a mass spectrometer include a MALDI-TOF (Matrix-Assisted Laser Desorption/Ionization-Time Of Flight) mass spectrometer, a MALDI-IT (Matrix-Assisted Laser Desorption/Ionization-Ion Trap) mass spectrometer, a MALDI-IT-TOF (Matrix-Assisted Laser Desorption/Ionization-Ion Trap-Time Of Flight) mass spectrometer, a MALDI-FTICR (Matrix-Assisted Laser Desorption/Ionization-Fourier Transform Ion Cyclotron Resonance) mass spectrometer, and the like.

EXAMPLES

Hereinbelow, the present invention will be specifically described with reference to the following examples, but is not limited to these examples.
3-AQ: 3-aminoquinoline
CA: p-coumaric acid ion
CHCA: α-cyano-4-hydroxycinnamic acid
2,5-DHB: 2,5-dihydroxybenzoic acid

Example 1

Analysis of Phosphorylated Peptides Using 3-AQ/CA (1) A 3-AQ solution that contained 100 nmol/μL of 3-AQ and 2 mM ammonium phosphate in an aqueous 50 (v/v) % acetonitrile (ACN) solution, and a CA solution that contained 100 nmol/μL of CA and 2 mM ammonium phosphate in an aqueous 50% (v/v) acetonitrile (ACN) solution were mixed in a ratio of 9:1 (v/v) to obtain a mixed solution. Then, the mixed solution was diluted 10-fold with an aqueous 50% (v/v) acetonitrile (ACN) solution containing 2 mM ammonium phosphate to prepare a 3-AQ/CA matrix solution.

(2) Aqueous 50% (v/v) ACN solutions containing 0.02 fmol/μL to 2,000 fmol/μL of commercially-available phosphorylated peptides β-casein 33-48 and β-casein 1-25 were prepared, respectively, by serially diluting the phosphorylated peptides with the same aqueous 50% (v/v) ACN solvent.

(3) Each of 0.5 μL of the 3-AQ/CA matrix solution prepared in (1) and 0.5 μL of the peptide sample solution prepared in (2) was dropped onto a MALDI plate (μFocus MALDI plate™, Hudson Surface Technology, Inc. USA) (on-target mix method).

(4) Analysis was performed by AXIMA Resonance (Shimadzu/Kratos, UK) in mid/high mass mode and in positive and negative modes. Then, detection limits were evaluated.

Comparative Example 1

Analysis of Phosphorylated Peptides Using 3-AQ/CHCA or 2,5-DHB (1) A DHB solution was prepared which contained 5 mg/0.5 mL of 2,5-DHB (Laser Bio) in an aqueous 50% (v/v) ACN solution. Further, 3-AQ (20 mg) was dissolved in 150 μL of a CHCA solution obtained by dissolving CHCA (10 mg) in 600 μL of an aqueous 50% (v/v) ACN solution, and the obtained solution was diluted 10-fold with an aqueous 50% (v/v) ACN solution containing 2 mM ammonium phosphate to prepare a 3-AQ/CHCA solution.

(2) Aqueous 50% (v/v) ACN solutions containing 0.02 fmol/μL to 2,000 fmol/μL of commercially-available phosphorylated peptides β-casein 33-48 and β-casein 1-25 were prepared, respectively, by serially diluting the phosphorylated peptides with the same aqueous 50% (v/v) ACN solvent.

(3) Each of 0.5 μL of the 2,5-DHB solution or the 3-AQ/CHCA solution prepared in (1) and 0.5 μL of the peptide sample solution prepared in (2) was dropped onto a MALDI plate (μFocus MALDI plate™, Hudson Surface Technology, Inc. USA) (on-target mix method).

(4) Analysis was performed by AXIMA Resonance (Shimadzu/Kratos, UK) in mid/high mass mode and in positive and negative modes. Then, detection limits were evaluated.

It is to be noted that the commercially-available phosphorylated peptides, β-casein 33-48 and β-casein 1-25 (both of which are manufactured by Sigma-Aldrich) are described in Table 1 in the above-mentioned Rapid Commun. Mass Spectrom., 2012, Vol. 26, pp. 2454-2460. pS represents a phosphorylated serine residue.

Bovine β-casein 33-48: Phosphorylation sites 1 (S35)

```
                                           (SEQ ID NO: 1)
         Sequence: FQ-pS-EEQQQTEDELQDK
```

Bovine β-casein 1-25: Phosphorylation sites 4 (S15, S17, S18, S19)

```
                                           (SEQ ID NO: 2)
         Sequence: RELEELNVPGEIVE-pS-L-pS-pS-pS-EESITR
```

TABLE 1

| | | Detection limit (fmol/well) | | |
|---|---|---|---|---|
| | | Example 1 | Comparative Example 1 | |
| | | 3-AQ/CA | 3-AQ/CHCA | 2,5-DHB |
| Positive | β-casein 33-48 | 1 | 1 | 1 |
| | β-casein 1-25 | 1 | 1 | 10 |
| Negative | β-casein 33-48 | 1 | 1 | 10 |
| | β-casein 1-25 | 1 | 1 | 10 |

Table 1 shows the detection limit of the molecular-related ion $[M+H]^+$ (positive mode) or $[M-H]^-$ (negative mode) of the phosphorylated peptide β-casein 33-48 or β-casein 1-25 when 3-AQ/CA, 3-AQ/CHCA, or 2,5-DHB was used as a matrix. As shown in Table 1, when the liquid matrix 3-AQ/CA was used, the detection limits in both positive and negative modes were 1 to 1/10, that is, sensitivity was improved 1- to 10-fold as compared to when 2,5-DHB or 3-AQ/CHCA was used.

FIG. 1 shows mass spectra of the phosphorylated peptide β-casein 1-25 in a concentration of 10 fmol/μL in positive mode when (A) 3-AQ/CA, (B) 3-AQ/CHCA, and (C) 2,5-DHB were used. From FIG. 1(A), (B), (C), when the liquid matrix 3-AQ/CA was used, the molecular-related ion [M+H]$^+$ of β-casein 1-25 was detected at a relatively higher ionic strength than the other ion species such as [M–H$_2$PO$_4$+H]$^+$ and [M–2H$_2$PO$_4$+H]$^+$ and at a high S/N ratio as compared to when 2,5-DHB or 3-AQ/CHCA was used. That is, when 3-AQ/CA was used, the desorption of a phosphate group during ionization was suppressed and measurement results were obtained with higher sensitivity as compared to when 2,5-DHB or 3-AQ/CHCA was used.

It is to be noted that a high-sensitive measurement equal to or better than that achieved by using 3-AQ/CHCA could be performed by using 3-AQ/CA. Therefore, the use of 3-AQ/CA makes it possible to perform a measurement by multistage MS with higher sensitivity.

Example 2

Analysis of Sugar Chains Using 3-AQ/CA (1) A 3-AQ solution that contained 100 nmol/μL of 3-AQ and 2 mM ammonium phosphate in an aqueous 50 (v/v) % acetonitrile (ACN) solution, and a CA solution that contained 100 nmol/μL of CA and 2 mM ammonium phosphate in an aqueous 50% (v/v) acetonitrile (ACN) solution were mixed in a ratio of 9:1 (v/v) to obtain a mixed solution. Then, the mixed solution was diluted 10-fold with an aqueous 50% (v/v) acetonitrile (ACN) solution containing 2 mM ammonium phosphate to prepare a 3-AQ/CA matrix solution.

(2) Aqueous solutions containing 0.04 fmol/μL to 4,000 fmol/μL of commercially-available PA-sugar chains NA2 glycan, NA4 glycan, A1 glycan, and A2 glycan (all of which are manufactured by Takara Bio Inc.) were prepared, respectively, by serially diluting the PA-sugar chains with the same water.

(3) The 3-AQ/CA matrix solution prepared in (1) and the sugar chain sample solution prepared in (2) were mixed in a ratio of 1:1 (v/v) (pre-mix method).

(4) Onto a MALDI plate (μFocus MALDI plate™, Hudson Surface Technology, Inc. USA) was dropped 0.5 μl of the sample/matrix mixed solution prepared in (3).

(5) Analysis was performed by AXIMA Resonance (Shimadzu/Kratos, UK) in mid mass mode and in positive and negative modes. Then, detection limits were evaluated.

Comparative Example 2

Analysis of Sugar Chains Using 3-AQ/CHCA or 2,5-DHB (1) A DHB solution was prepared which contained 5 mg/0.5 mL of 2,5-DHB (Laser Bio) in an aqueous 50% (v/v) ACN solution. Further, 3-AQ (20 mg) was dissolved in 150 μL of a CHCA solution obtained by dissolving CHCA (10 mg) in 600 μL of an aqueous 50% (v/v) ACN solution, and the obtained solution was diluted 10-fold with an aqueous 50% (v/v) ACN solution containing 2 mM ammonium phosphate to prepare a 3-AQ/CHCA solution.

(2) Aqueous solutions containing 0.04 fmol/μL to 4,000 fmol/μL of commercially-available PA-sugar chains NA2 glycan, NA4 glycan, A1 glycan, and A2 glycan (all of which are manufactured by Takara Bio Inc.) were prepared, respectively, by serially diluting the PA-sugar chains with the same water.

(3) The 2,5-DHB solution or the 3-AQ/CHCA solution prepared in (1) and the sugar chain sample solution prepared in (2) were mixed in a ratio of 1:1 (v/v) (pre-mix method).

(4) Onto a MALDI plate (μFocus MALDI plate™, Hudson Surface Technology, Inc. USA) was dropped 0.5 μL of the sample/matrix mixed solution prepared in (3).

(5) Analysis was performed by AXIMA Resonance (Shimadzu/Kratos, UK) in mid mass mode and in positive and negative modes. Then, detection limits were evaluated.

TABLE 2

| | | Detection limit (fmol/well) | | |
| | | Example 2 | Comparative Example 2 | |
| | | 3-AQ/CA | 3-AQ/CHCA | 2,5-DHB |
|---|---|---|---|---|
| Positive | NA2 glycan | 0.1 | 1 | 1 |
| | NA4 glycan | 1 | 1 | 10 |
| | A1 glycan | 1 | 1 | 10 |
| | A2 glycan | 1 | 1 | 100 |
| Negative | NA2 glycan | 1 | 1 | 10 |
| | NA4 glycan | 1 | 1 | 10 |
| | A1 glycan | 0.1 | 0.1 | 100 |
| | A2 glycan | 1 | 1 | 100 |

Table 2 shows the detection limit of the molecular-related ion [M+H]$^+$ (positive mode) or [M–H]$^-$ (negative mode) of the PA-sugar chain NA2 glycan, NA4 glycan, A1 glycan, or A2 glycan when 3-AQ/CA, 3-AQ/CHCA, or 2,5-DHB was used as a matrix. As shown in Table 2, when the liquid matrix 3-AQ/CA was used, the detection limits in both positive and negative modes were 1 to 1/1,000, that is, sensitivity was improved 1- to 1,000-fold as compared to when 2,5-DHB or 3-AQ/CHCA was used.

Figure 2:
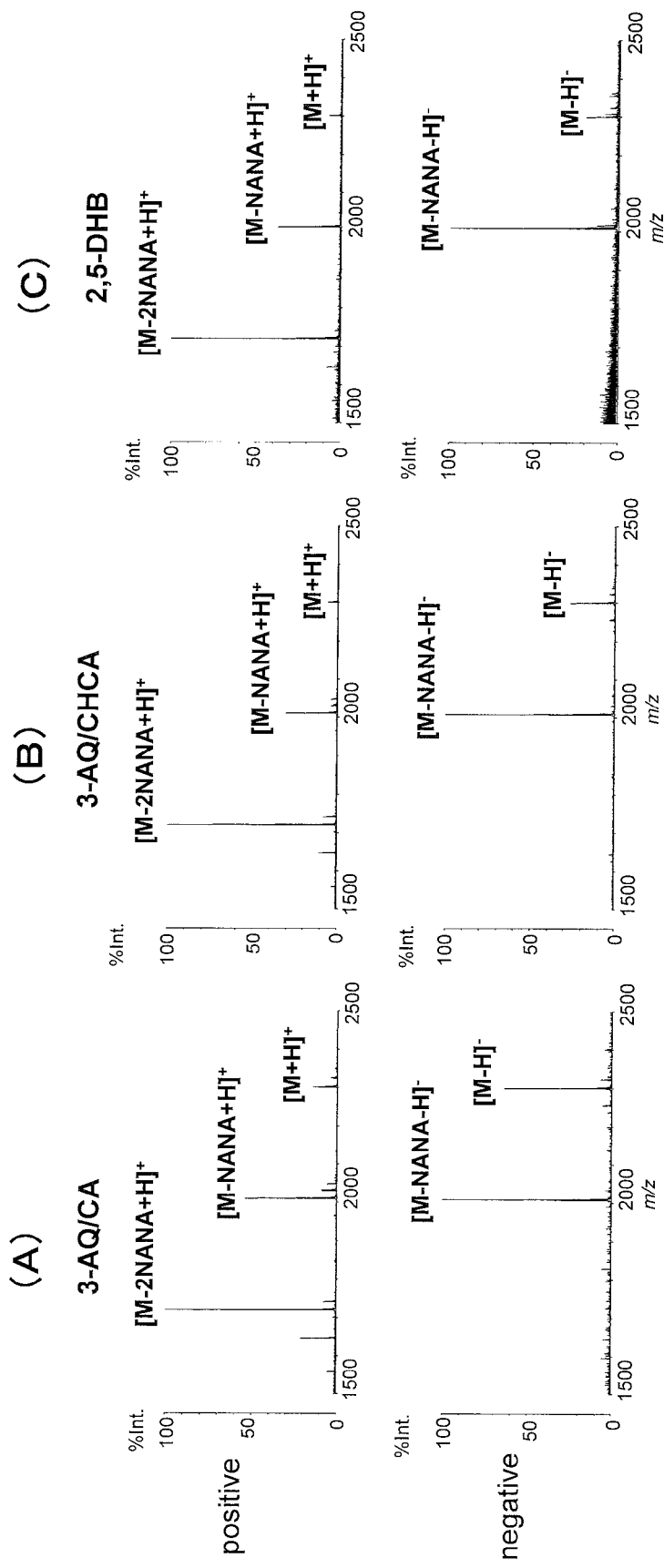
FIG. 2 shows mass spectra of a sugar chain A2 glycan in a concentration of 100 fmol/μL in positive mode (upper side) and negative mode (lower side) when (A) a liquid matrix 3-AQ/CA was used in Example 2, (B) 3-AQ/CHCA was used as a matrix in Comparative Example 2, and (C) 2,5-DHB was used as a matrix in Comparative Example 2, wherein a horizontal axis represents mass/charge (m/z) and a vertical axis represents a relative ionic strength (% Int.)

FIG. 2 shows mass spectra of A2 glycan in a concentration of 100 fmol/μL in positive mode (upper side) and negative mode (lower side) when (A) 3-AQ/CA, (B) 3-AQ/CHCA, and (C) 2,5-DHB were used. In FIG. 2, "NANA" represents sialic acid. From FIG. 2(A), (B), (C), when the liquid matrix 3-AQ/CA was used, the molecular-related ions [M+H]$^+$ (positive mode) and [M–H]$^-$ (negative mode) of A2 glycan were detected more clearly at a high S/N ratio as compared to when 2,5-DHB or 3-AQ/CHCA was used.

That is, as can be seen from, for example, the mass spectra in negative mode, when 3-AQ/CA was used, the highest relative ionic strength of the molecular-related ion [M–H]$^-$ relative to the sialic acid-desorbed ion [M-NANA-H]$^-$ was obtained.

As described above, when 3-AQ/CA was used, the desorption of an acidic sugar, sialic acid during ionization was suppressed as compared to when 2,5-DHB or 3-AQ/CHCA was used.

Figure 3:
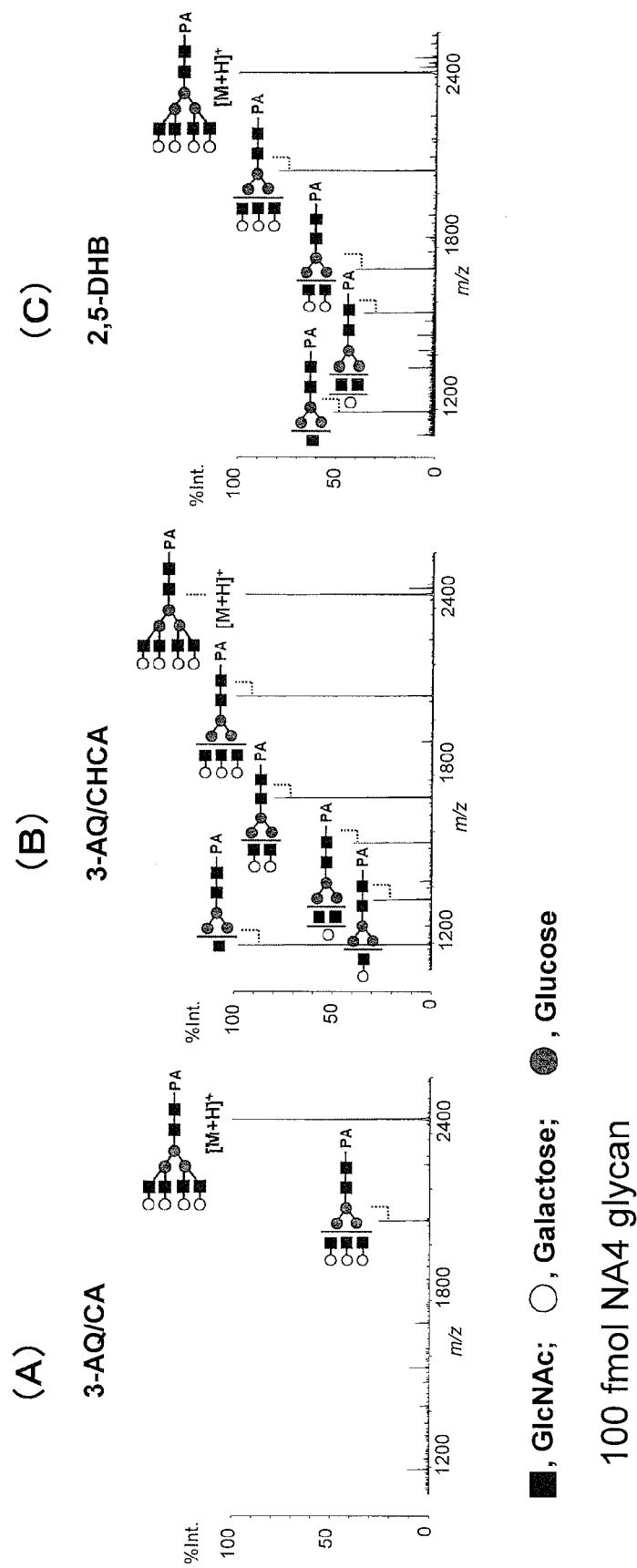
FIG. 3 shows mass spectra of a sugar chain NA4 glycan in a concentration of 100 fmol/μL in positive mode when (A) a liquid matrix 3-AQ/CA was used in Example 2, (B) 3-AQ/CHCA was used as a matrix in Comparative Example 2, and (C) 2,5-DHB was used as a matrix in Comparative Example 2, wherein a horizontal axis represents mass/charge (m/z) and a vertical axis represents a relative ionic strength (% Int.).

FIG. 3 shows mass spectra of NA4 glycan in a concentration of 100 fmol/μL in positive mode when (A) 3-AQ/CA, (B) 3-AQ/CHCA, and (C) 2,5-DHB were used. From FIG. 3(A), (B), (C), when the liquid matrix 3-AQ/CA was used, the molecular-related ion [M+H]$^+$ (positive mode) of NA4 glycan was detected at a relatively higher ionic strength than the other ion species derived from sugar chain desorption and at a high S/N ratio as compared to when 2,5-DHB or 3-AQ/CHCA was used. That is, when 3-AQ/CA was used, the desorption of a neutral sugar during ionization was suppressed as compared to when 2,5-DHB or 3-AQ/CHCA was used.

It is to be noted that a high-sensitive measurement equal to or better than that achieved by using 3-AQ/CHCA could be performed by using 3-AQ/CA. Therefore, the use of 3-AQ/CA makes it possible to perform a measurement by multistage MS with higher sensitivity.

What is claimed is:

1. A method for mass spectrometry of phosphorylated peptides or sugar chains, the method comprising using, as a liquid matrix, an ionic liquid comprising a 3-aminoquinoline ion and a p-coumaric acid ion.

2. The method for mass spectrometry of phosphorylated peptides or sugar chains according to claim 1, wherein the liquid matrix comprising 3-aminoquinoline and p-coumaric acid in a molar ratio of 5:1 to 20:1.

3. The method for mass spectrometry of phosphorylated peptides or sugar chains according to claim 1, wherein ammonium phosphate is used as an additive.

* * * * *